US010265134B2

(12) United States Patent
Munson

(10) Patent No.: US 10,265,134 B2
(45) Date of Patent: Apr. 23, 2019

(54) SURGICAL DRAPE FOR FLUID COLLECTION

(71) Applicant: Erik A. Munson, Minnetrista, MN (US)

(72) Inventor: Erik A. Munson, Minnetrista, MN (US)

(*) Notice: Subject to any disclaimer, the term of this patent is extended or adjusted under 35 U.S.C. 154(b) by 446 days.

(21) Appl. No.: 15/006,729

(22) Filed: Jan. 26, 2016

(65) Prior Publication Data

US 2016/0213439 A1 Jul. 28, 2016

Related U.S. Application Data

(60) Provisional application No. 62/125,619, filed on Jan. 26, 2015.

(51) Int. Cl.
| | |
|---|---|
| *A61B 46/00* | (2016.01) |
| *A61B 46/27* | (2016.01) |
| *A61B 46/20* | (2016.01) |
| *A61B 46/23* | (2016.01) |

(52) U.S. Cl.
CPC ............ *A61B 46/30* (2016.02); *A61B 46/27* (2016.02); *A61B 2046/201* (2016.02); *A61B 2046/205* (2016.02); *A61B 2046/236* (2016.02)

(58) Field of Classification Search
CPC ......... A61B 46/00; A61B 46/20; A61B 46/27; A61B 46/30; A61B 2046/201; A61B 2046/205; A61B 2046/236
USPC ................................................. 128/849, 856
See application file for complete search history.

(56) References Cited

U.S. PATENT DOCUMENTS

| | | | | |
|---|---|---|---|---|
| 2,715,902 | A * | 8/1955 | Shaffer | A61B 46/30 128/853 |
| 5,419,343 | A * | 5/1995 | Taylor | A61B 46/00 128/849 |
| 5,445,165 | A * | 8/1995 | Fenwick | A61B 46/00 128/849 |
| 5,916,202 | A * | 6/1999 | Haswell | A61M 1/0236 128/849 |
| 6,070,586 | A | 6/2000 | Harroll | |
| 2016/0081751 | A1* | 3/2016 | Marshburn | A61B 46/30 128/854 |

FOREIGN PATENT DOCUMENTS

WO 2014/197306 A1 12/2014

OTHER PUBLICATIONS

3M Catalog—Product Description—Under Buttocks Drape with Pouch—3M™ Steri-Drape™ 7984, Jan. 16, 2016, 1 page.
Halyard Health Catalog—Product Descriptions—89584—Halyard Basics* Under Buttocks Drape with Pouch, Sterile, 79584—Halyard Basics* Under Buttocks Drape with Pouch, Non-Sterile, etc., Jan. 16, 2016, 8 pages.

* cited by examiner

*Primary Examiner* — Keri J Nelson
(74) *Attorney, Agent, or Firm* — Quarles & Brady LLP

(57) ABSTRACT

The present invention is directed to a surgical drape that provides for effective and fluid collection while reducing the reducing the risk of staff or patient contact with fluid expelled from a patient during a medical procedure.

9 Claims, 5 Drawing Sheets

SURGICAL DRAPE FOR FLUID COLLECTION

CROSS-REFERENCE TO RELATED APPLICATIONS

This application claims the benefit of U.S. Provisional Patent Application No. 62/125,619, filed Jan. 26, 2015, which is incorporated herein by reference as if set forth in its entirety.

STATEMENT AS TO RIGHTS TO INVENTIONS MADE UNDER FEDERALLY SPONSORED RESEARCH AND DEVELOPMENT

Not applicable.

BACKGROUND

A surgical drape is the usual means employed for provision of a barrier between a surgical site and other fields during surgery or another medical procedure. Surgical drapes are also employed for such purposes as maintaining sterility of the surgical site and reducing potentially hazardous exposure of medical personnel to fluids expelled from the patient. While many prior art drapes are configured to minimize contact to non-sterile fields and to shield medical personnel from exposure to body fluid expelled during medical procedures, these devices do not incorporate a means for effectively collecting, retaining, or measuring expelled fluid.

For certain medical procedures, such as pelvic surgical procedures (e.g., hysteroscopy, cystoscopy), it is imperative that medical personnel monitor and accurately measure fluid being pumped into and expelled from a patient. For example, over-absorption of fluid used to distend a body cavity such as the uterus can result in shock or intoxication of the patient. Accordingly, there remains a need in the art for improved surgical drapes that provide for more effective and accurate fluid collection and measurement.

SUMMARY

In a first aspect, provided herein is a surgical drape comprising an under-buttocks panel; a first leg pocket configured to receive the right leg of the patient; a second leg pocket configured to receive the left leg of the patient; and a filtered collection reservoir configured for fluid collection, where the under-buttocks panel and an interior seam of each of the first and second pockets are integrally formed with a collection panel comprising an opening in fluid communication with the filtered collection reservoir.

In some cases, the drape further comprises an adhesive strip disposed on a distal aspect of the under-buttocks panel, configured for removable adhesion to a lower back or upper buttocks region of the patient.

In some cases, the drape further comprises an adhesive strip disposed at a proximal aspect of the collection panel, configured for removable adhesion to a person performing a medical procedure.

The drape can further comprise a cover panel configured to cover at least a portion of the patient's body, and defining an opening configured to provide access to a sterile field for a medical procedure. The filtered collection reservoir can comprise a screen. The filtered collection reservoir can comprise a port. In some cases, the filtered collection reservoir is at least partially transparent to permit a user to view the fluid within the container. The filtered collection reservoir can comprise graduated marks for measuring the volume or change in volume of a fluid within the filtered collection reservoir. The graduated marks can be located at predetermined positions such that the graduated marks denote approximate volumes.

Further areas of applicability of the present teachings will become apparent from the description provided herein. It should be understood that the description and specific examples are intended for purposes of illustration only and are not intended to limit the scope of the present teachings.

BRIEF DESCRIPTION OF THE DRAWINGS

The present invention will be better understood and features, aspects and advantages other than those set forth above will become apparent when consideration is given to the following detailed description thereof.

Corresponding reference numerals indicate corresponding parts throughout the several views of drawings.

DETAILED DESCRIPTION

The following description is of the best mode presently contemplated for carrying out the invention. This description is not to be taken in a limiting sense, but is made merely for the purpose of describing one or more preferred embodiments of the invention. The scope of the invention should be determined with reference to the claims.

In General

As used herein, the term "about" means within 5% of a stated length, width, amount, concentration, concentration range, or stated time frame.

It must be noted that as used herein and in the appended claims, the singular forms "a," "an," and "the" include plural reference unless the context clearly dictates otherwise. As well, the terms "a" (or "an"), "one or more" and "at least one" can be used interchangeably herein. It is also to be noted that the terms "comprising," "including," and "having" can be used interchangeably.

Unless defined otherwise, all technical and scientific terms used herein have the same meanings as commonly understood by one of ordinary skill in the art to which this invention belongs. All references cited in this specification are to be taken as indicative of the level of skill in the art. Nothing herein is to be construed as an admission that the invention is not entitled to antedate such disclosure by virtue of prior invention.

Surgical drapes described herein provide an effective and convenient method of collecting and controlling fluids. Such surgical drapes are particularly advantageous for effective collection and accurate measurement of fluids during obstetric, gynecological, or other medical procedures. Procedures appropriate for use of the surgical drapes provided herein include, without limitation, hysteroscopy, cystoscopy, urology, proctology, and childbirth. Although several embodiments described herein refer to fluid control and collection associated with hysteroscopy and cystoscopy, embodiments of the described invention may be used to collect fluid used in or discharged from the patient during other medical procedures.

Figure 1:
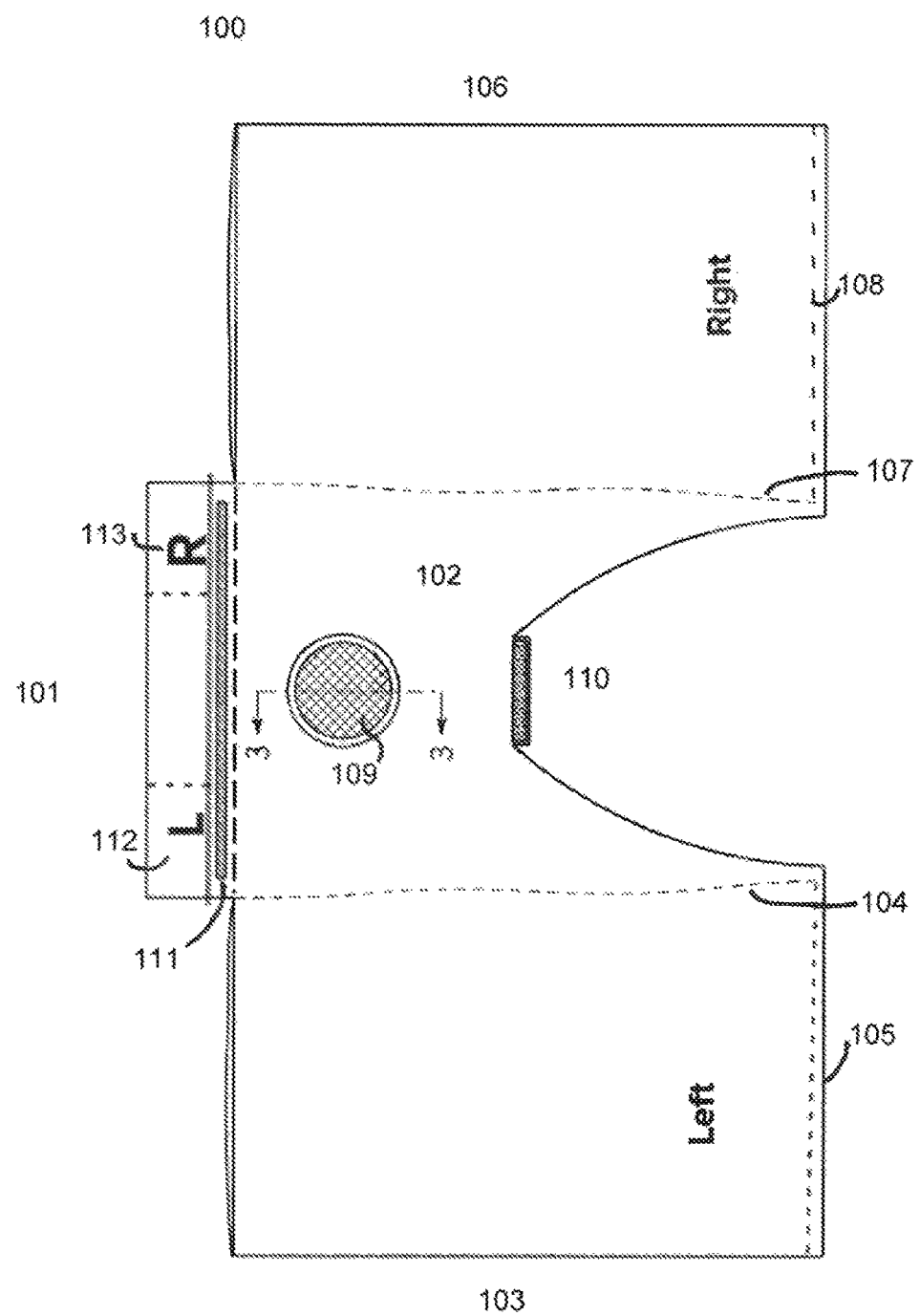
FIG. 1 is a top plan view of an exemplary surgical drape configured for effective fluid collection in accordance with an exemplary embodiment of the present disclosure.

FIG. 1 illustrates one embodiment of a surgical drape provided herein. Referring to FIG. 1, the present disclosure provides a surgical drape 100 comprising an under-buttocks panel 101 and leg pockets 103 and 106 configured to individually receive the patient's right and left legs. Preferably, the under-buttocks panel 101 and interior seams 104 and 107 of each of the leg pockets are integrally formed with a collection panel 102 comprising an opening 109 in fluid communication with a filtered collection reservoir 114 configured for fluid collection. In preferred embodiments, first leg pocket 103 and second leg pocket 106 comprise seams (105 and 108) at the proximal end (foot end) of each leg pocket, as well as interior seams 104 and 107) adjacent to the collection panel, thus creating two individual "pant legs" configured to receive and cover each leg and to maintain a sterile field. Preferably, the leg pockets cover each leg from hip to toe.

Figure 2:
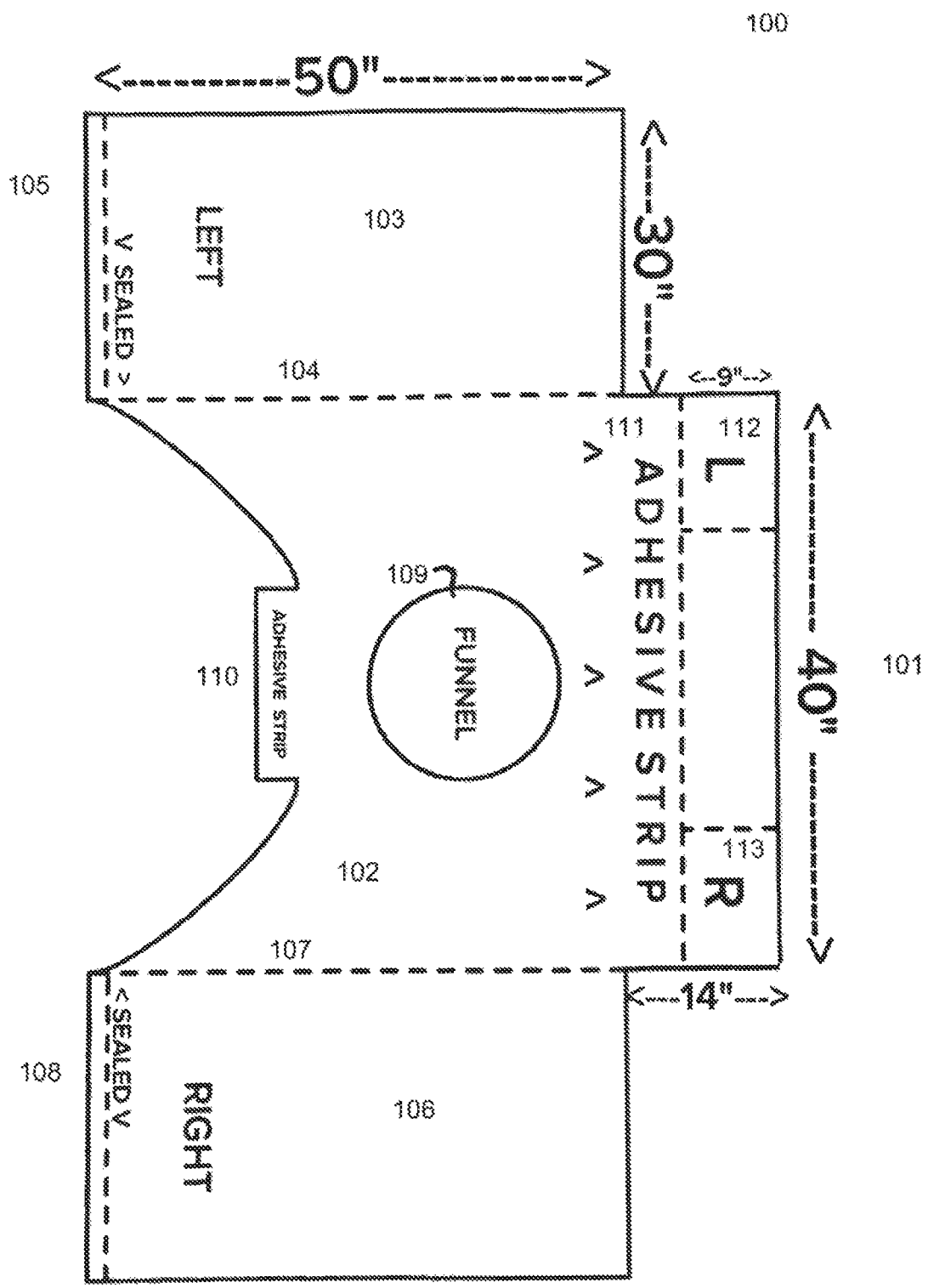
FIG. 2 is a top plan view of exemplary surgical drape configured for effective fluid collection in accordance with an alternative embodiment.

Referring now to FIGS. 1 and 2, exemplary embodiments of a surgical drape 100 provided herein further comprise a first leg pocket 103 configured to receive the right leg of the patient; and a second leg pocket 106 configured to receive the left leg of the patient. In some cases, the under-buttocks panel 101 and an interior seam of each of the first and second leg pockets 104 and 107 are integrally formed with a collection panel 102 comprising an opening 109. When integrally formed, the under-buttocks drape 101, leg pockets 103 and 106, and collection panel 102 form one large drape.

In some cases, the surgical drape further includes one or more indicia symbolically directing placement of the drape. For example, the surgical drape can include an "end of table" indicator to provide guidance for effective orientation, placement, or alignment of the drape relative to, for example, an examination table, the patient, and the person forming the medical procedure. Symbolic placement indicia can include, without limitation, lines, hash marks, dashed lines, arrows, arrowheads, letters, numbers, characters, words, etc. In some cases, symbolic placement indicia include nested symbols. Placement indicia may be any indicia capable of being affixed to the drape and readily visible. Further, the indicia may be removably or permanently affixed to the drape by processes including, without limitation, glue or other adhesive material, formed as part of the drape, painted, drawn or imprinted on the drape, or any other known affixation method.

In exemplary embodiments, the under-buttocks panel 101 comprises a left-hand 112 pocket and a right-hand 113 pocket configured to permit the surgeon or another medical professional to place the under-buttocks panel beneath the patient without contamination. Advantageously, by deploying and positioning a surgical drape 100 utilizing leg pockets 103 and 106 and/or hand pockets, the surgeon's hands and surgical tools do not contact unsterile skin of the patient. Note that the pockets shown in FIGS. 1-2 are illustrative in size, shape, and placement only. It will be clear to those of ordinary skill in the art having the benefit of this disclosure that other sizes, shapes, and placements are also possible.

Figure 3:
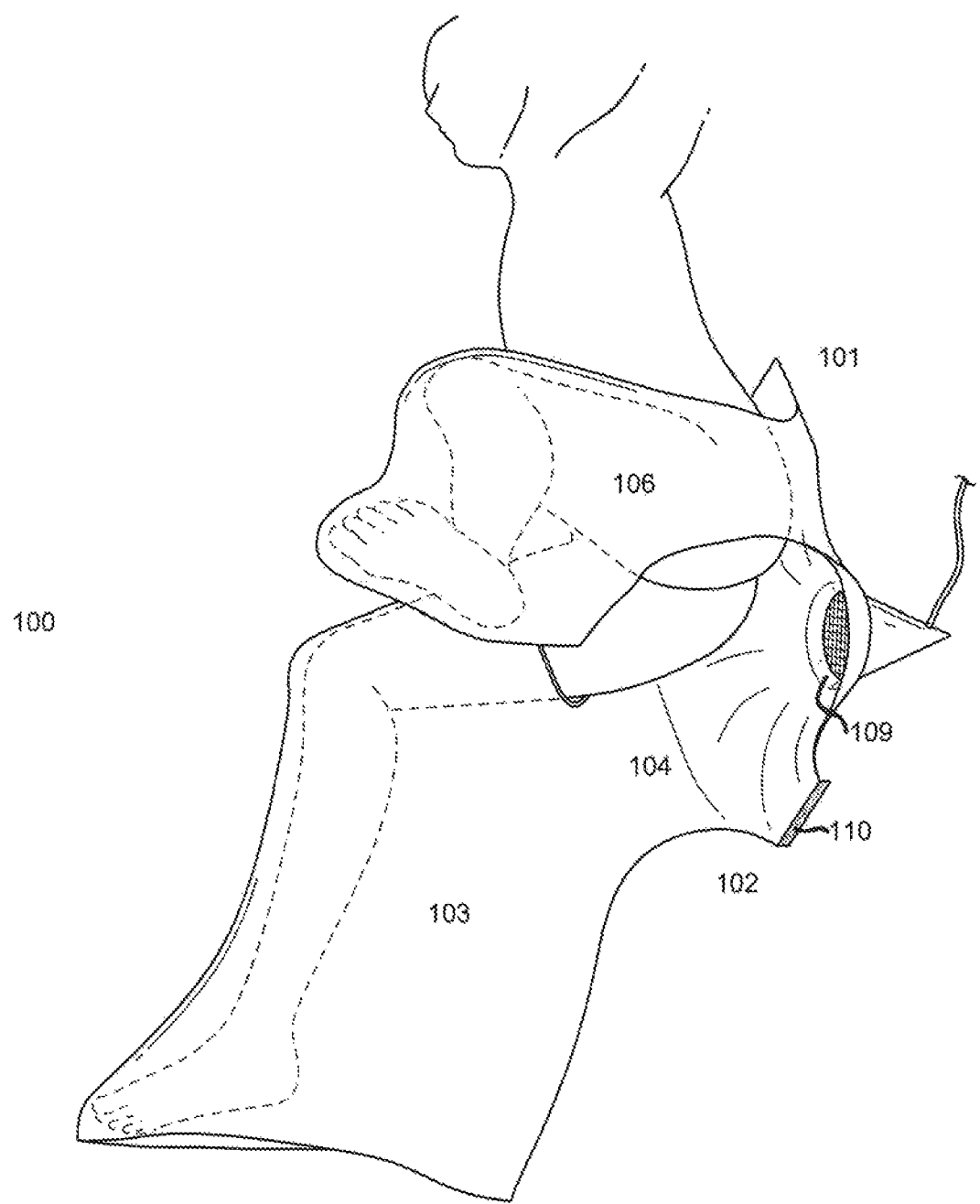
FIG. 3 illustrates a perspective view of a surgical drape in use with a patient in the lithotomy position, demonstrating placement of the under-buttocks panel, collection panel, and graduated reservoir in accordance with an exemplary embodiment of the present disclosure.

FIG. 3 illustrates features of a surgical drape 100 of the present disclosure when utilized with a patient in the lithotomy position. The medical term "lithotomy position" refers to a common position for surgical procedures and medical examinations in obstetrics, urology, gynecology, proctology, and other procedures involving the pelvis or lower abdomen. A patient in the lithotomy position is positioned on his or her back with hips and knees flexed and the thighs apart. Referring to FIG. 3, the under-buttocks panel 101 of a surgical drape 100 is configured for placement under and behind the patient's buttocks. As described in further detail below, the under-buttocks panel is configured to be attached to the dorsal (back) side of the patient's body, preferably at a lower back region or distal to the gluteal cleft.

Figure 4:
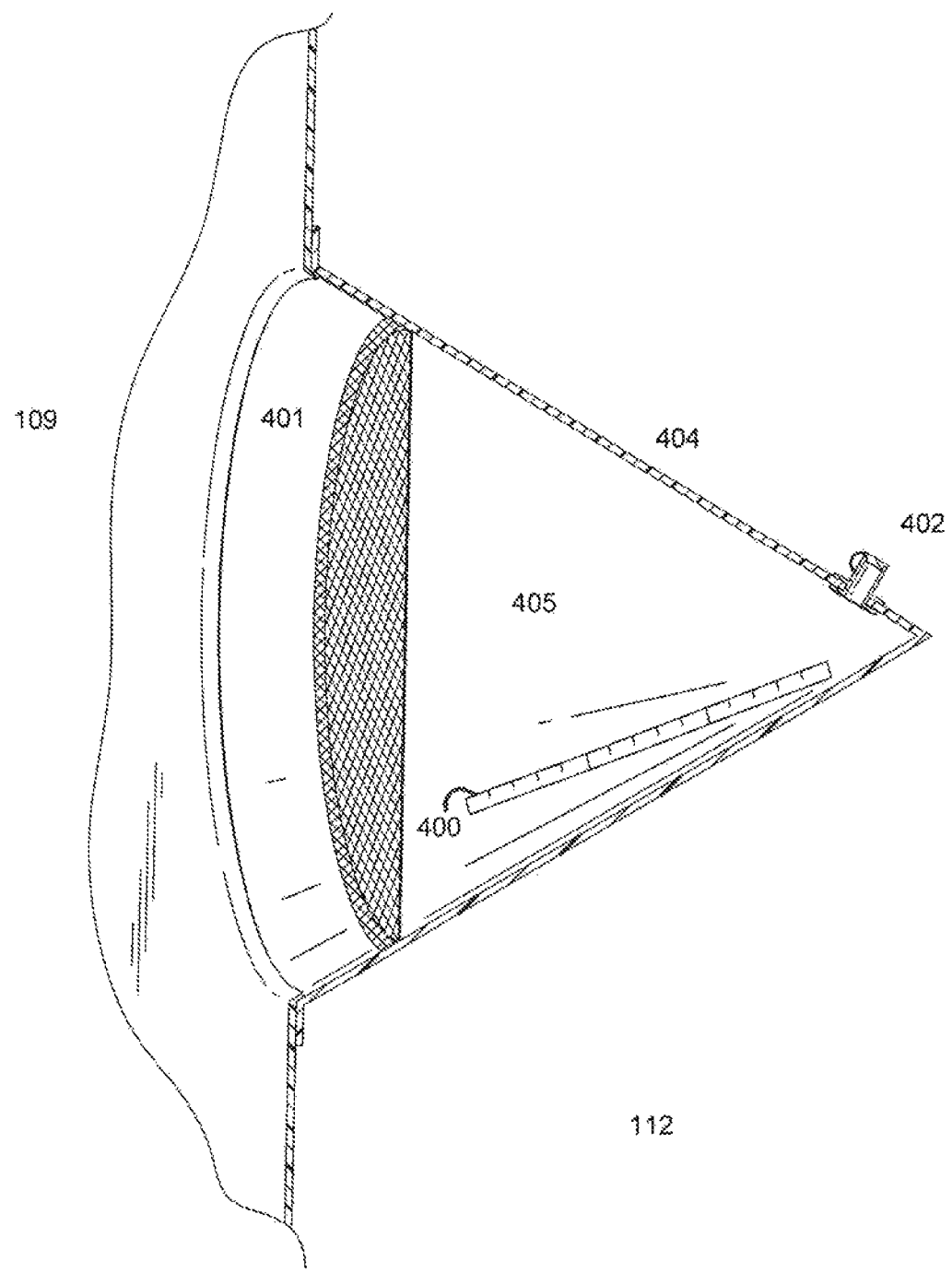
FIG. 4 illustrates a side-view cross section of a graduated reservoir with a close-up view of the edges of the collection panel in accordance with an exemplary embodiment of the present disclosure.

Surgical drapes provided herein further comprise a filtered collection reservoir in fluid communication with a filtered collection reservoir 114 configured for fluid collection. In exemplary embodiments, the filtered collection reservoir 114 comprises a full collection funnel 404 and a screen or filter 401. Referring to FIGS. 3 and 4, the screen or filter 401 can be disposed within the filtered collection reservoir 114 and in proximity to the opening 109 defined by the collection panel 102. The screen or filter 401 is configured to catch solid or semi-solid materials and prevent such materials from collecting in the body of the filtered collection reservoir 114.

Figure 5:
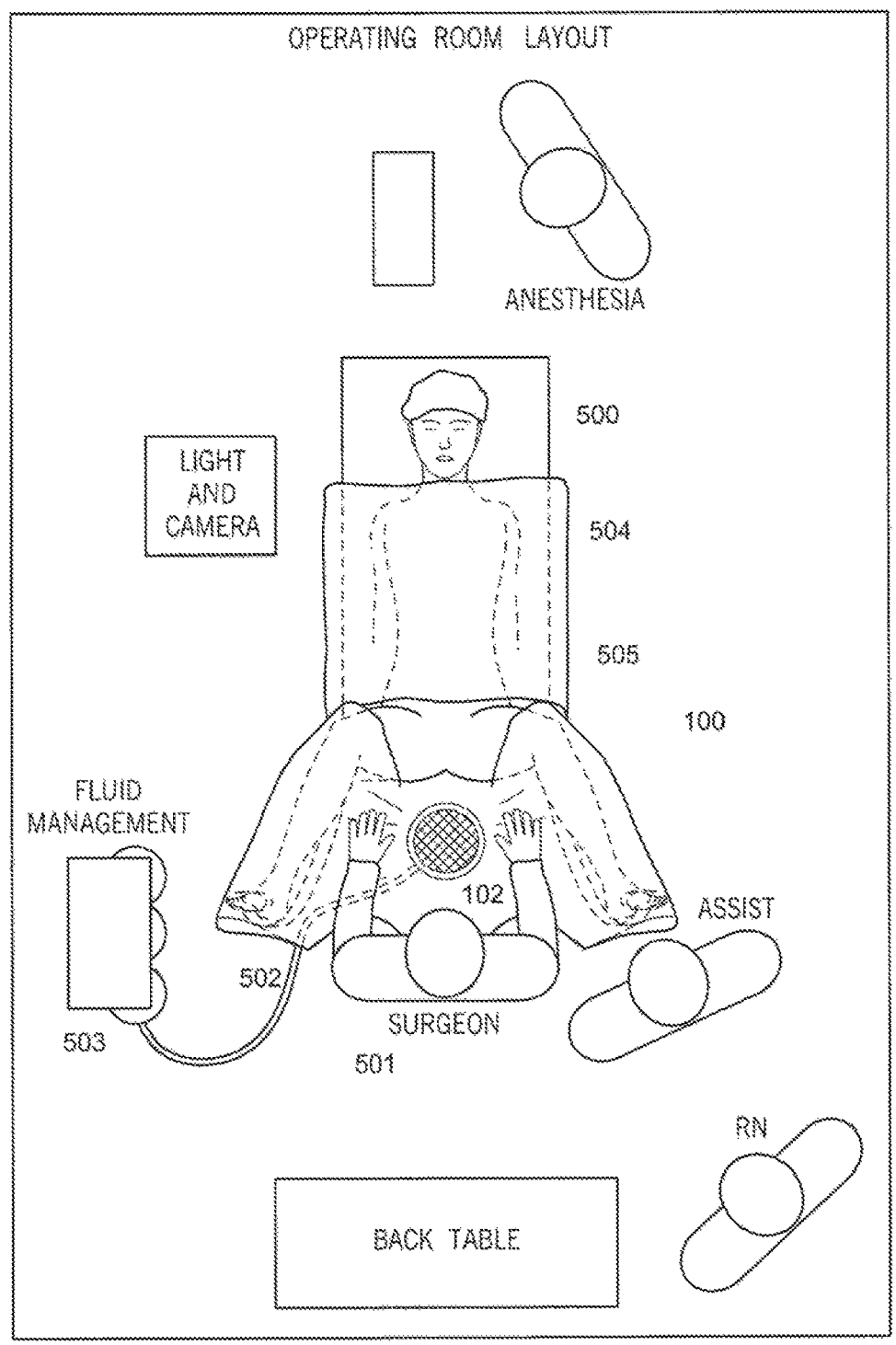
FIG. 5 illustrates a surgical drape in use with a patient in a generic operating room layout in accordance with an exemplary embodiment of the present disclosure.

For use of a surgical drape as provided herein in connection with a fluid management system, the filtered collection reservoir 114 comprises a port 402. Referring to FIGS. 4 and 5, the filtered collection reservoir can comprise a port 402 in communication with the interior portion 405 of the reservoir 114, and connectable at a proximal end with a tube for conducting fluid for collection outside of the reservoir. In some cases, a port is placed toward a tapered end of the filtered collection reservoir and is configured for attachment to suction tubing 502 in communication with a fluid management system 403. As used herein, the term "fluid management system" refers to a system or apparatus configured to pump and measure fluid (e.g., distension fluid) introduced into a patient and to measure the volume of fluid expelled from the patient.

Referring to FIG. 4, the filtered collection reservoir 114 can additionally or alternatively comprise graduated marks 400 for measuring the volume or change in volume of a fluid within the collection container. Such graduated marks 400 provide a fluid measuring scale when the surgical drape is not used in connection with a fluid management system, or when the fluid management system has malfunctioned. Graduated marks 400 and are preferably located at predetermined positions such that the graduated marks denote approximate volumes of fluid contained therein. In exemplary embodiments, the filtered collection reservoir 114 is at least partially transparent to permit a user to view the fluid within the funnel portion 405 of the reservoir and determine fluid volume as indicated by graduated marks.

The graduated reservoir is preferably made of a flexible, fluid-impermeable material. For example, the graduated reservoir can be a flexible bag. It may be advantageous in some cases to include an adhesive closure or other closure suitable to retain fluids within the graduated reservoir following use of the drape.

Referring to FIG. 5, in some cases, the surgical drape 100 further comprises a cover panel 504 that covers at least a ventral (i.e., belly side) portion of the patient 500, and that defines an opening 505 configured to provide a surgeon or other medical personnel 501 with access for performing a medical procedure. For example, the cover panel 504 can provide access to the pelvic region for performing a hysteroscopy.

Advantageously, surgical drapes provided herein are effective for accurately accounting for fluid leaving the patient during a procedure which reduces risks, mortality, and morbidity associated with inaccurate fluid control and accounting. For example, exemplary embodiments, the surgical drape 100 further comprises one or more adhesive strips disposed at distal and/or proximal portions of the surgical drape. As used herein, the terms "distal" and "distally" refer to a location farthest from the surgeon or other medical professional performing the medical procedure. The terms "proximal" and "proximally" refer to a location closest to the surgeon or other medical professional performing the medical procedure. For example, referring to FIG. 2, an adhesive strip 111 can disposed on the back side of the distal portion of the under-buttocks panel 101. In such cases, the adhesive strip 111 is operable to removably adhere the distal portion of the under-buttocks panel 101 of the surgical drape 100 to the lower back or upper buttocks region of the patient such that the drape is held in place and provides a backstop or barrier to retain fluids that may collect beneath the patient. Accordingly, the under-buttocks panel adhesive strip 111 operates such that the drape will not readily move, slide, or otherwise be easily displaced from beneath the patient.

Referring to FIGS. 3 and 5, the surgical drape 100 provided herein can optionally include one or more adhesive strips 110 disposed on the back side of the proximal portion of the collection panel 102 of a surgical drape. In such cases, the collection panel adhesive strip 110 is operable to removably adhere to a surgeon 401 or other medical professional such that the collection panel 102 is held in place without interfering with the surgeon's hands or tools. Preferably, such an adhesive strip 110 is configured to bring the collection panel 102 into direct contact with the clothing or protective wear worn by a surgeon 501 or other medical professional (e.g., the front of a medical professional's scrubs or lab coat). In this manner, the collection panel 102 slopes from the point of removable adhesion to the surgeon 501, forming a trough or basin for fluid collection, directing fluid toward the opening 109 and into a filtered collection reservoir 114 via the collection panel 102, and preventing exposure of the surgeon or medical professional from fluid such as, for example, fluid expelled from the patient during the medical procedure. Placement of the collection panel adhesive strip 110 can be determined based on factors such as, for example, the surgeon's height, size, and personal preferences.

Any suitable surgical or medical adhesive material can be used for the adhesive strips. An adhesive strip can be sprayed, brushed, rolled or otherwise disposed directly onto the back side of the drape. Alternatively, an adhesive strip can be a strip of double-sided tape disposed on the back side of a portion of the drape prior to or at the time of use. In some cases, a strip of removable non-adhesive backing material such as, for example, waxed or coated paper can be placed over an adhesive portion of the adhesive strip to preserve viability of the adhesive strip until use of surgical drape. At the time of use or just prior to use, the removable non-adhesive backing can be removed to expose an adhesive portion. Once the non-adhesive backing is removed, the adhesive strip can be contacted to the patient or the practitioner as described herein.

Any suitable material can be used in the production of a surgical drape provided herein. In exemplary embodiments, the surgical drape is made of a thin, flexible material. Such material can be a non-absorbent, non-woven, fluid impermeable material such as plastic. Preferably, the plastic comprises polyethylene. A surgical drape 100 can be manufactured using other materials including, without limitation, various non-woven or woven materials, blends of polyester, polypropylene, polyethylene, and urethane, or combinations thereof. These materials and methods are illustrative only, as others will be readily apparent to those of ordinary skill in the art having the benefit of this disclosure. For example, one or more antimicrobial layers can be added to further enhance antimicrobial protection.

The surgical drape is preferably constructed by heat sealing seams. In exemplary embodiments, the surgical drape comprises or consists essentially of disposable materials such that, after use, most or all of the surgical drape can be discarded.

Illustrative dimensions now are provided to further describe one embodiment suitable for use for fluid collection. For example, referring to FIG. 5, a surgical drape of the present disclosure can have an overall dimension of about 100 inches wide and about 50" long, where the under-buttocks panel has a width of about 40 inches, and where each leg pocket has a width of about 30 inches. It will be clear to those of ordinary skill in the art having the benefit of this disclosure that these dimensions are examples only, provided to present a clearer image of one embodiment, and can readily be modified based upon application or customer demand.

While the invention has been described in the foregoing specifications with reference to details of the illustrated embodiments, these details are not intended to limit the scope of the invention as by the appended claims.

I claim:
1. A surgical drape comprising
an under-buttocks panel;
a first leg pocket configured to receive the right leg of the patient;
a second leg pocket configured to receive the left leg of the patient, wherein an interior region of each of said first and second leg pockets is integrally formed with a collection panel, wherein interior seams of each of said first and second leg pockets are connected to said collection panel along the entire length of each interior seam; and
a filtered collection reservoir within said collection panel, the filtered collection reservoir comprising a circular opening for accepting fluid from the under-buttocks panel and first and second leg pockets, and a funnel shape configured for fluid collection;
whereby the under-buttocks panel, each of said first and second leg pockets, and the collection panel form an integrated surgical drape in fluid communication with the circular opening of the filtered collection reservoir, the collection panel thereby configured to direct any fluid retained beneath the patient and retained along interior seams of the first and second leg pockets into the filtered collection reservoir.
2. The drape of claim 1, further comprising an adhesive strip disposed on a distal aspect of the under-buttocks panel, configured for removable adhesion to a lower back or upper buttocks region of the patient.

3. The drape of claim 1, further comprising an adhesive strip disposed at a proximal aspect of the collection panel, configured for removable adhesion to a person performing a medical procedure.

4. The drape of claim 1, further comprising a cover panel, configured to cover at least a portion of the patient's body, and defining an opening configured to provide access to a sterile field for a medical procedure.

5. The drape of claim 1, wherein the filtered collection reservoir comprises a screen.

6. The drape of claim 1, wherein the filtered collection reservoir comprises a port.

7. The drape of claim 1, wherein the filtered collection reservoir is at least partially transparent to permit a user to view fluid collected therein.

8. The drape of claim 1, wherein the filtered collection reservoir comprises graduated marks for measuring the volume or change in volume of a fluid within the filtered collection reservoir.

9. The drape of claim 8, wherein the graduated marks are located at predetermined positions such that the graduated marks denote approximate volumes.

\* \* \* \* \*